US010743845B2

(12) United States Patent
Kanayama et al.

(10) Patent No.: US 10,743,845 B2
(45) Date of Patent: Aug. 18, 2020

(54) ULTRASOUND DIAGNOSTIC APPARATUS AND METHOD FOR DISTINGUISHING A LOW SIGNAL/NOISE AREA IN AN ULTRASOUND IMAGE

(71) Applicant: Toshiba Medical Systems Corporation, Otawara-shi (JP)

(72) Inventors: Yuko Kanayama, Nasushiobara (JP); Naohisa Kamiyama, Utsunomiya (JP)

(73) Assignee: Canon Medical Systems Corporation, Otawara-shi (JP)

( * ) Notice: Subject to any disclaimer, the term of this patent is extended or adjusted under 35 U.S.C. 154(b) by 424 days.

(21) Appl. No.: 14/139,009

(22) Filed: Dec. 23, 2013

(65) Prior Publication Data

US 2014/0114189 A1    Apr. 24, 2014

Related U.S. Application Data

(63) Continuation of application No. PCT/JP2012/065857, filed on Jun. 21, 2012.

(30) Foreign Application Priority Data

Jun. 23, 2011 (JP) ................................. 2011-139654

(51) Int. Cl.
*A61B 8/08* (2006.01)
*A61B 8/00* (2006.01)
(Continued)

(52) U.S. Cl.
CPC ............ *A61B 8/5269* (2013.01); *A61B 8/463* (2013.01); *A61B 8/485* (2013.01); *A61B 8/5246* (2013.01);
(Continued)

(58) Field of Classification Search
None
See application file for complete search history.

(56) References Cited

U.S. PATENT DOCUMENTS

| 8,382,669 B2 | 2/2013 | Kakee | |
| 2003/0158479 A1* | 8/2003 | Li | .................... G01S 7/52046 600/437 |

(Continued)

FOREIGN PATENT DOCUMENTS

| JP | S60-31740 A | 2/1985 |
| JP | S63-130054 A | 6/1988 |

(Continued)

OTHER PUBLICATIONS

International Search Report dated Sep. 25, 2012 for PCT/JP2012/065857 filed Jun. 21, 2012 with English Translation.

(Continued)

*Primary Examiner* — Amelie R Davis
(74) *Attorney, Agent, or Firm* — Oblon, McClelland, Maier & Neustadt, L.L.P.

(57) ABSTRACT

According to an embodiment, an analyzer analyzes the state of a tissue at a position in a subject from which an ultrasound wave that is transmitted by an ultrasound probe into the subject is reflected, the analysis being on the basis of a received signal of the ultrasound wave. A signal acquiring unit acquires noises signal information corresponding to an area that is analyzed by the analyzer. A noise area extracting unit determines, regarding each area analyzed by the analyzer, whether the received signal that is used for the analysis performed by the analyzer is a noise signal, the determination being on the basis of the noise signal information acquired by the signal acquiring unit. A display controller configured controls a display unit such that the display unit displays an area regarding which the area (Continued)

extracting unit determines that the received signal is a noise signal.

8 Claims, 9 Drawing Sheets

(51) Int. Cl.
    *G01S 7/52*     (2006.01)
    *G01S 15/89*     (2006.01)

(52) U.S. Cl.
    CPC ...... *G01S 7/52026* (2013.01); *G01S 7/52036* (2013.01); *G01S 7/52046* (2013.01); *G01S 15/8952* (2013.01); *A61B 8/488* (2013.01); *G01S 7/52071* (2013.01); *G01S 7/52074* (2013.01)

(56) References Cited

U.S. PATENT DOCUMENTS

| | | | |
|---|---|---|---|
| 2004/0133104 A1 | 7/2004 | Cohen-Bacrie et al. | |
| 2004/0260180 A1* | 12/2004 | Kanai | A61B 5/02007 600/449 |
| 2008/0249405 A1* | 10/2008 | Kakee | A61B 8/08 600/437 |
| 2009/0076387 A1 | 3/2009 | Simopoulos | |
| 2010/0134629 A1* | 6/2010 | Lindop | A61B 8/08 348/163 |
| 2010/0220901 A1* | 9/2010 | Matsumura | A61B 8/08 382/128 |
| 2010/0249590 A1 | 9/2010 | Kanayama et al. | |
| 2010/0331698 A1* | 12/2010 | Tonomura | A61B 8/0833 600/443 |
| 2011/0026800 A1* | 2/2011 | Tonomura | A61B 5/7264 382/131 |
| 2011/0245676 A1* | 10/2011 | Lin | A61B 8/5269 600/447 |
| 2012/0209115 A1* | 8/2012 | Tonomura | A61B 8/08 600/438 |

FOREIGN PATENT DOCUMENTS

| | | |
|---|---|---|
| JP | 4-210053 A | 7/1992 |
| JP | H07-051270 A | 2/1995 |
| JP | 8-322838 A | 12/1996 |
| JP | 2001-238884 A | 9/2001 |
| JP | 2002-209899 A | 7/2002 |
| JP | 2002-301069 A | 10/2002 |
| JP | 2004-528921 A | 9/2004 |
| JP | 2005-118152 A | 5/2005 |
| JP | 2006-326178 A | 12/2006 |
| JP | 2008-073423 A | 4/2008 |
| JP | 2008-136880 A | 6/2008 |
| JP | 2008-253549 A | 10/2008 |
| JP | 2009-066420 A | 4/2009 |
| JP | 2010-233859 A | 10/2010 |

OTHER PUBLICATIONS

International Written Opinion dated Sep. 25, 2012 for PCT/JP2012/065857 filed Jun. 21, 2012.

Office Action dated May 26, 2015 in Japanese Patent Application No. 2011-139654.

Japanese Office Action dated Dec. 15, 2015 in Patent Application No. 2011-139654 (without English Translation).

* cited by examiner

FIG.6
(A) 2MHz-IMAGE
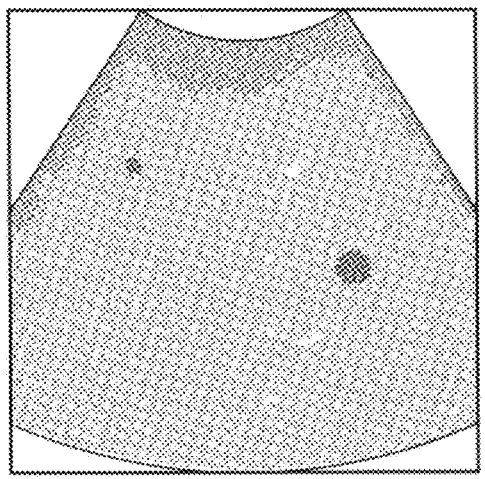
(B) 4MHz-IMAGE
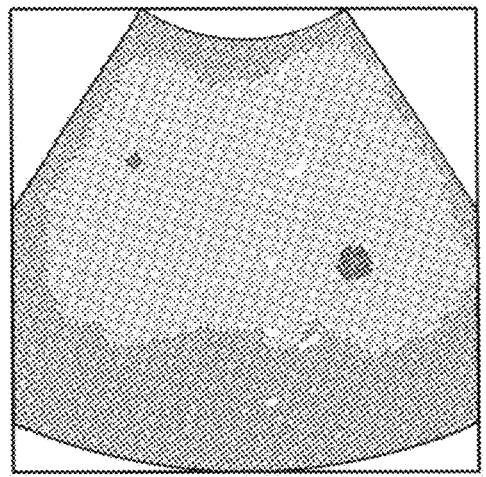
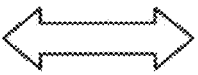
DIFFERENCE
(C) SUPERPOSED IMAGE OF 4MHz-IMAGE AND ATTENUATION IMAGE
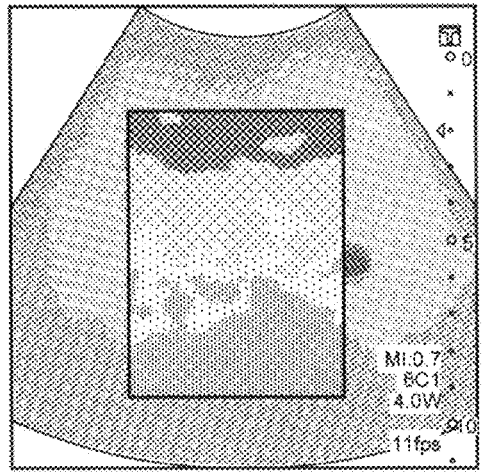
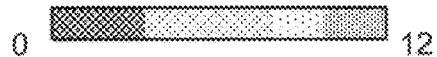
0　　　　　　　　　　　　12

FIG.8
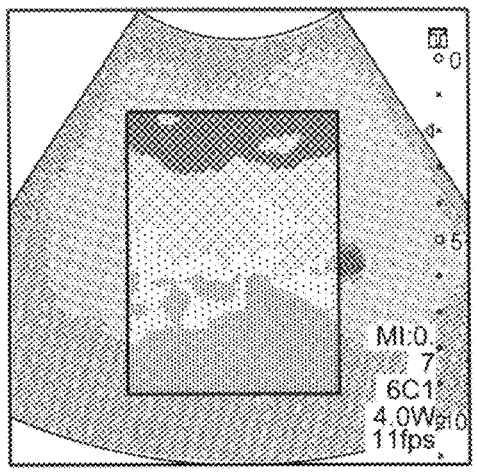
(A) SUPERPOSED IMAGE OF 4MHz-IMAGE AND ATTENUATION IMAGE
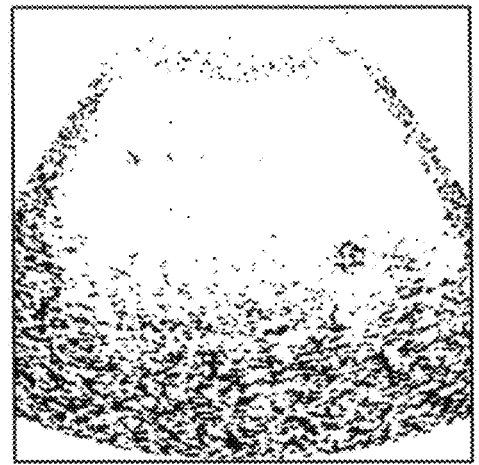
(B) LOW S/N AREA IN 4MHz-IMAGE
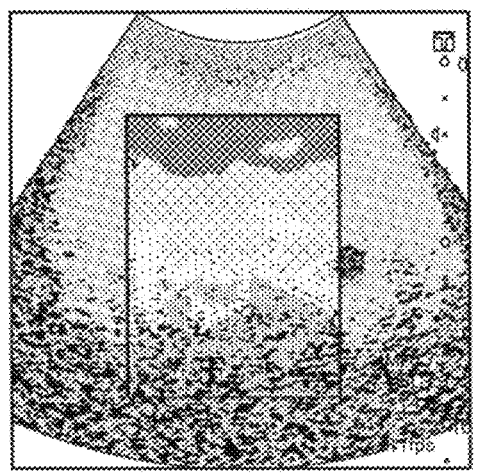
(C) SUPERPOSED IMAGE

| TRANSMITTING/RECEIVING CONDITION | | | NOISE SIGNAL |
|---|---|---|---|
| FREQUENCY | TRANSMISSION FOCUS | GAIN | |
| | | | |
| | | | |
| | | | |
| | | | |

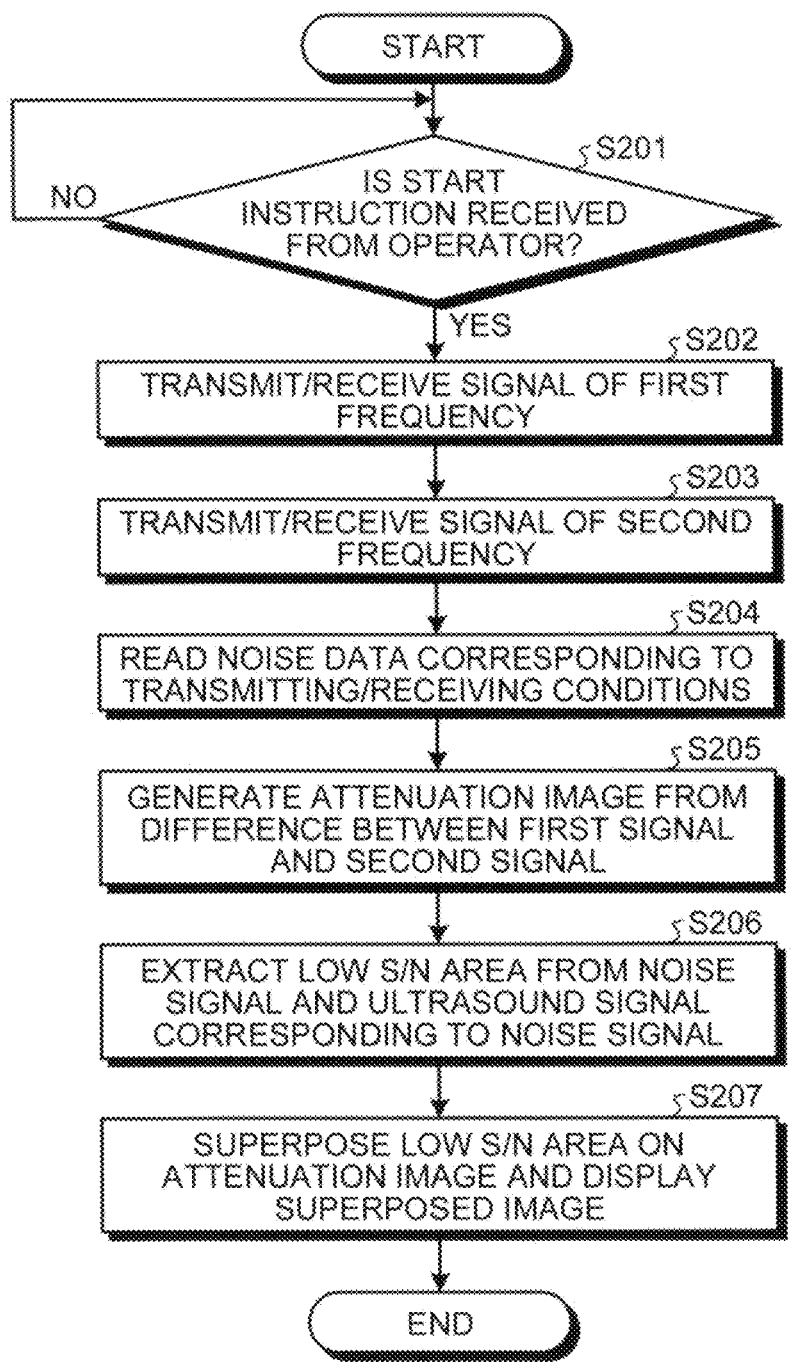

ULTRASOUND DIAGNOSTIC APPARATUS AND METHOD FOR DISTINGUISHING A LOW SIGNAL/NOISE AREA IN AN ULTRASOUND IMAGE

CROSS-REFERENCE TO RELATED APPLICATIONS

This application is a continuation of International Application No. PCT/JP2012/065857, filed on Jun. 21, 2012 which claims the benefit of priority of the prior Japanese Patent Application No. 2011-139654, filed on Jun. 23, 2011, the entire contents of which are incorporated herein by reference.

FIELD

Embodiments described herein relate generally to an ultrasound diagnostic apparatus and a method.

BACKGROUND

In present-day medical treatments, conventional ultrasound diagnostic apparatuses are used for examining and diagnosing various body tissues, such as the heart, liver, kidney, and mammary glands, and these medical image diagnostic apparatuses are advantageous with respect to ease of operability and non-invasiveness as well as being without radiation risks when compared to other medical image diagnostic apparatuses, such as X-ray diagnostic apparatuses and X-ray computed tomography apparatuses.

Ultrasound diagnostic apparatuses usually visualize the morphology of a body tissue by expressing the amplitude of a received signal (echo signal) of an ultrasound wave in luminance. It has been reported in various reports that an echo signal contains various types of physical information, and some of this physical information has clinical applications.

For example, an ultrasound signal with which a subject is irradiated propagates through the subject while attenuating. If the amount of attenuation is large, a phenomenon occurs where the echo signal cannot be received sufficiently. Observation of the characteristics of body tissue by observing such attenuation of an echo signal is often performed and various methods are known in which the amount of attenuation of an echo signal is quantitatively analyzed and then used for diagnosis. However, with the above-described conventional technology, an area that is difficult to reliably analyze may also be analyzed by using the physical information contained in an echo signal.

BRIEF DESCRIPTION OF THE DRAWINGS

FIG. 6 is a diagram illustrating an exemplary process performed by an analyzer according to the first embodiment;

FIG. 8 is a diagram illustrating an exemplary process performed by a display controller according to the first embodiment;

FIG. 11 is a flowchart of a procedure of a process performed by an ultrasound diagnostic apparatus according to the second embodiment.

DETAILED DESCRIPTION

First Embodiment

According to an embodiment, an ultrasound diagnostic apparatus includes an analyzer, an acquiring unit, a determining unit and a display controller. The analyzer configured to analyze the state of a tissue at a position in a subject from which an ultrasound wave that is transmitted by an ultrasound probe into the subject is reflected, the analysis performed by the analyzer being on the basis of a received signal of the ultrasound wave. The acquiring unit configured to acquire noise signal information corresponding to an area that is analyzed by the analyzer. The determining unit configured to determine, regarding each area analyzed by the analyzer, whether the received signal that is used for the analysis performed by the analyzer is a noise signal, the determination performed by the determining unit being on the basis of the noise signal information acquired by the acquiring unit. The display controller configured to control a display unit such that the display unit displays an area regarding which the determining unit determines that the received signal is a noise signal.

Figure 1:
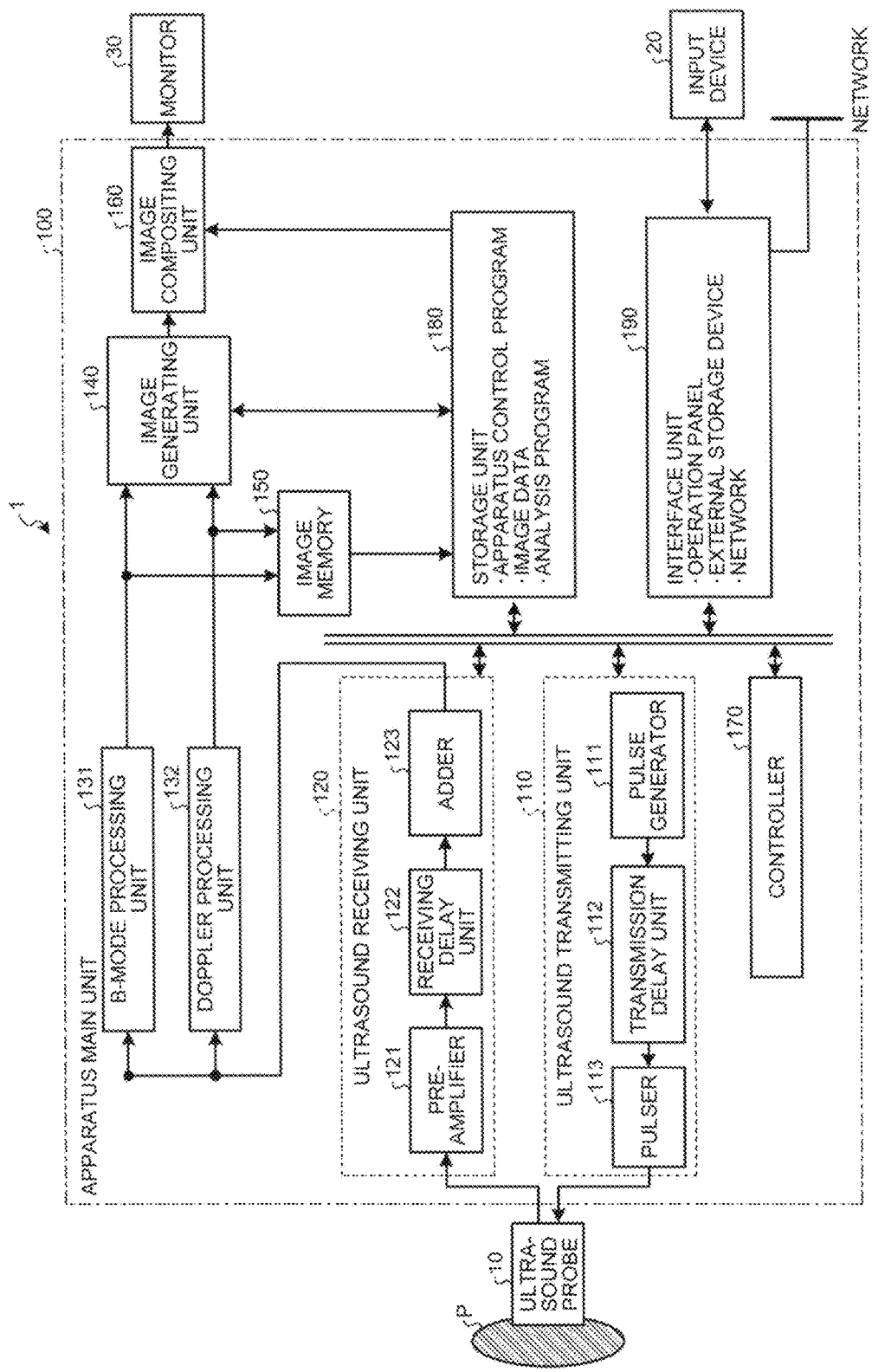
FIG. 1 is a diagram illustrating an overall configuration of an ultrasound diagnostic apparatus according to a first embodiment.

First, a configuration of an ultrasound diagnostic apparatus according to a first embodiment will be described. FIG. 1 is a diagram illustrating an overall configuration of an ultrasound diagnostic apparatus according to the first embodiment. As shown in FIG. 1, an ultrasound diagnostic apparatus 1 according to the first embodiment includes an ultrasound probe 10, an input device 20, a monitor 30, and an apparatus main unit 100.

The ultrasound probe 10 includes multiple piezoelectric vibrators and the piezoelectric vibrators generate ultrasound waves according to a drive signal that is supplied from an ultrasound transmitting unit 110 of the apparatus main unit 100, which is described below. The ultrasound probe 10 receives a reflected-wave signal from a subject P and converts the signal to an electric signal. The ultrasound probe 10 includes a matching layer with which the piezoelectric vibrators are provided and a backing material that prevents backward propagation of ultrasounds from the piezoelectric vibrators. The ultrasound probe 10 is detachably connected to the apparatus main unit 100.

When an ultrasound wave is transmitted from the ultrasound probe 10 to a subject P, the transmitted ultrasound wave is sequentially reflected from a surface in the body tissue of the subject P on which there is a discontinuity in the acoustic impedance and is received as a reflected-wave signal by the piezoelectric vibrators of the ultrasound probe 10. The amplitude of the received reflected-wave signal depends on the acoustic impedance difference on the discontinuity surface from which the ultrasound wave is reflected. The reflected-wave signal as a result of reflection of a transmitted ultrasound pulse from, for example, the moving blood flow or the surface of the cardiac wall, according to the Doppler effect, depends on the speed component of the moving object in the direction in which the ultrasound wave is transmitted and is affected by frequency transition.

The first embodiment can be used in the following two cases: when the ultrasound probe 10 that is a one-dimensional ultrasound probe in which multiple piezoelectric vibratos are linearly arranged scans a subject P two-dimensionally; and when the ultrasound probe 10 that mechanically vibrates multiple piezoelectric vibrators of a one-dimensional ultrasound probe or the ultrasound probe 10 that is two-dimensional ultrasound probe in which multiple piezoelectric vibrators are two-dimensionally arranged in matrix scans the subject P three-dimensionally.

The input device 20 is connected to the apparatus main unit 100. The input device 20 includes a mouse, a keyboard, a button, a panel switch, a touch command screen, a foot-switch, and a track ball. The input device 20 receives various setting requests from the operator of the ultrasound diagnostic apparatus 1 and transfers various received setting requests to the apparatus main unit 100. For example, the input device 20 receives a request for setting a region of interest (ROI) or a request for setting a color gain from the operator.

The monitor 30 displays a graphical user interface (GUI) for the operator of the ultrasound diagnostic apparatus 1 to input various setting requests by using the input device 20 or displays an ultrasound image that is generated by the apparatus main unit 100. Specifically, the monitor 30 displays, as an image, in-vivo morphological information and in-vivo blood-flow information on the basis of video signals that are input from an image compositing unit 160 described below.

The apparatus main unit 100 generates an ultrasound image on the basis of the reflected-wave signal that is received by the ultrasound probe 10. As shown in FIG. 1, the apparatus main unit 100 includes the ultrasound transmitting unit 110, an ultrasound receiving unit 120, a B-mode processing unit 131, a Doppler processing unit 132, an image generating unit 140, an image memory 150, the image compositing unit 160, a controller 170, a storage unit 180, and an interface unit 190.

The ultrasound transmitting unit 110 includes a pulse generator 111, a transmission delay unit 112, and a pulser 113. The ultrasound transmitting unit 110 supplies a drive signal to the ultrasound probe 10. The pulse generator 111 repeatedly generates a rate pulse for forming an ultrasound wave to be transmitted at a predetermined frequency. The transmission delay unit 112 provides each rate pulse generated by the pulse generator 111 with a delay time necessary for each piezoelectric vibrator to focus the ultrasound waves that are generated by the ultrasound probe 10 into a beam and to determine its transmitting directionality. The pulser 113 applies a drive signal (drive pulse) to the ultrasound probe 10 at a timing based on the rate pulse. The transmission direction or the delay time for determining a transmission direction is stored in the storage unit 180 and the transmission delay unit 112 refers to the storage unit 180 and provides the delay time.

The ultrasound receiving unit 120 includes a pre-amplifier 121, an analog/digital (A/D) converter (not shown), a receiving delay unit 122, and an adder 123. The ultrasound receiving unit 120 generates reflected-wave data by performing various processes on the reflected-wave signal received by the ultrasound probe 10. The pre-amplifier 121 amplifies the reflected-wave signal for each channel. The A/D converter (not shown) performs an A/D conversion on the amplified reflected-wave signal. The receiving delay unit 122 provides a delay time necessary to determine the receiving directionality. The adder 123 generates reflected-wave data by performing an add process on the reflected-wave signal processed by the receiving delay unit 122. The add process performed by the adder 123 increases the reflection component in the direction corresponding to the receiving directionality of the reflected-wave signal and forms a combined beam of ultrasound transmitting/receiving according to the receiving directionality and transmitting directionality. As in the case of transmitting, the receiving direction or a delay time for determining the receiving direction is stored in the storage unit 180 and the receiving delay unit 122 refers to the storage unit 180 to supply a delay time.

The ultrasound transmitting unit 110 and the ultrasound receiving unit 120 control the transmitting directionality and receiving directionality of ultrasound transmitting/receiving. The ultrasound transmitting unit 110 and the ultrasound receiving unit 120 have a function of quickly changing the delay information, the transmission frequency, the transmission drive voltage, and the number of aperture devices under the control of the controller 170 described below. Particularly, the transmission drive voltage can be changed by using a linear-amplifier oscillation circuit that can switch the value or a mechanism that electrically switches between multiple power supply units. The ultrasound transmitting unit 110 may transmit a different waveform for each frame or each rate and the ultrasound receiving unit 120 may receive the waveform.

The B-mode processing unit 131 receives, from the ultrasound receiving unit 120, the reflected-wave data that is the processed reflected-wave signal on which the gain correction process, the A/D conversion process, and the add the process have been performed, and the B-mode processing unit 131 then generates data (B-mode data) in which the signal intensity is expressed as luminance by performing logarithmic amplification and an envelope detection process.

The Doppler processing unit 132 performs a frequency analysis on the speed information on the basis of the reflected-wave data received from the ultrasound receiving unit 120, extracts, according to the Doppler effect, blood flow, tissue, and contrast agent echo components, and generates data (Doppler data) obtained by extracting moving object information, such as an average speed, dispersion, and power at multiple points.

The image generating unit 140 generates an ultrasound image from the B-mode data generated by the B-mode processing unit 131 and the Doppler data generated by the Doppler processing unit 132 and stores the generated ultrasound image in the image memory 150 or the storage unit 180 described below.

Specifically, the image generating unit 140 generates a B-mode image in which the signal intensity is expressed as luminance from the B-mode data. The image generating unit 140 generates, from blood-flow information, a color Doppler image in which power components indicating blood flow speed, dispersion, and the amount of blood flow are displayed such that they can be identified by color.

The image generating unit 140 converts (scan convert) a scanning-line signal array for ultrasound scanning to a scanning-line signal array of a video format represented by TV and generates an ultrasound image (a B-mode image and a color Doppler image) as a display image.

The image memory 150 stores image data, such as contrast images or tissue images that are generated by the image generating unit 140. The image memory 150 stores the result of a process performed by the image generating unit 140 described below. The image memory 150 further stores, as required, an output signal (radio frequency: RF) just after being output from the ultrasound receiving unit 120, a luminance signal of an image, various types of raw data, and image data acquired via a network. The data format of image data stored in the image memory 150 may be a data format after a video format conversion for displaying on the monitor 30 by the controller 170, which is described below, or a data format before a coordinate conversion that is raw data generated by the B-mode processing unit 131 and the Doppler processing unit 132.

The image compositing unit 160 generates a composite image obtained by compositing an ultrasound image generated by the image generating unit 140 with character information on various parameters, scales, and body marks. The composite image generated by the image compositing unit 160 is displayed on the monitor 30.

The controller 170 is a control processor (central processing unit: CPU) that performs functions of the information processing device (computer). The controller 170 controls whole processes of the ultrasound diagnosing apparatus 1. Specifically, on the basis of various instructions and setting requests that are input by the operator via the input device 20 and various programs and various setting information that are read from the storage unit 180, the controller 170 controls processes performed by the ultrasound transmitting unit 110, the ultrasound receiving unit 120, the B-mode processing unit 131, the Doppler processing unit 132, the image generating unit 140, and the image compositing unit 160 and performs a control such that ultrasound images stored in the image memory 150 are displayed on the monitor 30.

The storage unit 180 stores various programs for transmitting/receiving an ultrasound wave and performing image processing and display processing and stores various types of data, such as diagnostic information (for example, a patient ID and a doctor's opinion) and diagnostic protocols, and various types of setting information. The various programs 181 may include a program in which a procedure for performing the same process as that performed by the controller 170 is described.

The storage unit 180 is also used to store ultrasound images that are stored in the image memory 150, if required. Various types of data stored in the storage unit 180 can be transferred to outer peripheral devices via the interface unit 190.

The interface unit 190 is an interface related to the input device 20, the operation panel, a new external storage device (not shown), and the network. Data, such as an ultrasound image acquired by the ultrasound diagnostic apparatus 1, can be transferred by the interface unit 190 to another device via the network.

The ultrasound transmitting unit 110 and the ultrasound receiving unit 120 that are incorporated in the apparatus main unit 100 may be configured as hardware, such as an integrated circuit, or may be achieved using a software-module program.

An overall configuration of the ultrasound diagnostic apparatus according to the first embodiment has been described above. The ultrasound diagnostic apparatus 1 according to the first embodiment is configured such that the process performed by the controller 170, which will be described in detail below, allows only areas that can be reliably analyzed using physical information contained in an echo signal.

First, a case of the conventional technology will be described in which areas that are difficult to reliably analyze are also analyzed using physical information contained in an echo signal. For example, the following methods of the conventional technology are known to be used for diagnosing by quantitatively analyzing the amount of attenuation of an echo signal. An exemplary method is known for estimating the amount of attenuation specific to a subject by transmitting multiple ultrasound pulses each having a different center frequency and by comparing the received signals that are acquired with regard to how much the intensity of the received signals changes in the depth direction. A method is also known for estimating the amount of attenuation specific to a target tissue by comparing multiple frequency signals with regard to the change in their intensity and utilizing the characteristic that the amount of attenuation of ultrasound waves in a living body depends on the frequency.

A method is also known for obtaining the same effects as those obtained by the above-described methods by transmitting/receiving a broadband ultrasound pulse without using multiple ultrasound pulses each having a different ultrasound wave. Furthermore, with respect to the above-described method, a method is also known for eliminating a high-frequency component that is generated during propagation by transmitting two ultrasound pulses whose polarity is inverted in a single direction in order to eliminate the difference resulting from the signal having a high-frequency component generated when a low-frequency signal propagates through the body tissue and by performing a difference operation on an acquired received signal.

A method has been also proposed in which signals of multiple frequency components obtained by the above-described various methods are used to perform a color display reflecting the amount of attenuation. For example, a method is proposed in which superposed display is performed by, for example, allocating different colors to multiple frequency components, respectively. This method allows the observer to accurately understand the amount of attenuation visually by observing the magnitude of change in hue in the depth direction. Furthermore, a method is also known in which an attenuation constant at each point on a cross section is calculated by performing a color mapping according to the signal intensity difference between two different frequency components and by performing a differentiation on the signal intensity difference between two frequency components in the depth direction and the magnitude of the calculated attenuation constants are colored accordingly. For example, by observing the amount of attenuation of a received signal from a liver by using the above-described method, fatty liver or cirrhosis can be doubted.

Each of the above-described methods estimates the amount of attenuation by calculating the signal intensity of a received signal. In order to perform estimation with high accuracy, it is necessary to accurately measure the signal intensity. However, the attenuation of an ultrasound signal differs for each frequency and, particularly, the attenuation is significant for high-frequency components. Accordingly, in a deep area to be observed, the signal-noise ratio (S/N) is small and thus the reliability of the measured signal intensity is reduced.

Specifically, when the S/N is small, the magnitude of the real signal intensity and the magnitude of the signal intensity of noise to be added thereto become equal. Thus, the measured amplitude of the signal and the luminance of a B-mode image are over-estimated. For example, because a change in the difference between the signal intensity of a low-frequency signal and the signal intensity of a high-frequency signal after a log compression increases proportionally to the attenuation constant (dB/cm/MHz) of a tissue to be observed, the attenuation constant of a tissue to be observed can be estimated from the change in the difference in the depth direction. However, because, in a deep area to be observed, the signal intensity of a high-frequency signal in which the attenuation is significant, as described above, is measured as an intensity higher than the real signal intensity, the difference between the low-frequency signal and the signal intensity becomes small, and accordingly the attenuation constant is underestimated.

Accordingly, even for a target having the same attenuation constant in reality, the result of estimating an attenuation constant varies if the S/N varies. For example, if the same tissue is scanned with different gains and an attenuation constant is estimated from each of the acquired signals, a signal of even a deep area of an observation target can be obtained if the gain of the image is generally large, and thus the S/N increases. However, when the gain of the image is low, a signal of only a shallow area is obtained that is not the same as in the case of the larger gain of the image, and thus the S/N in the deep area becomes low. As a result, the result of estimating an attenuation constant varies.

Figure 2:
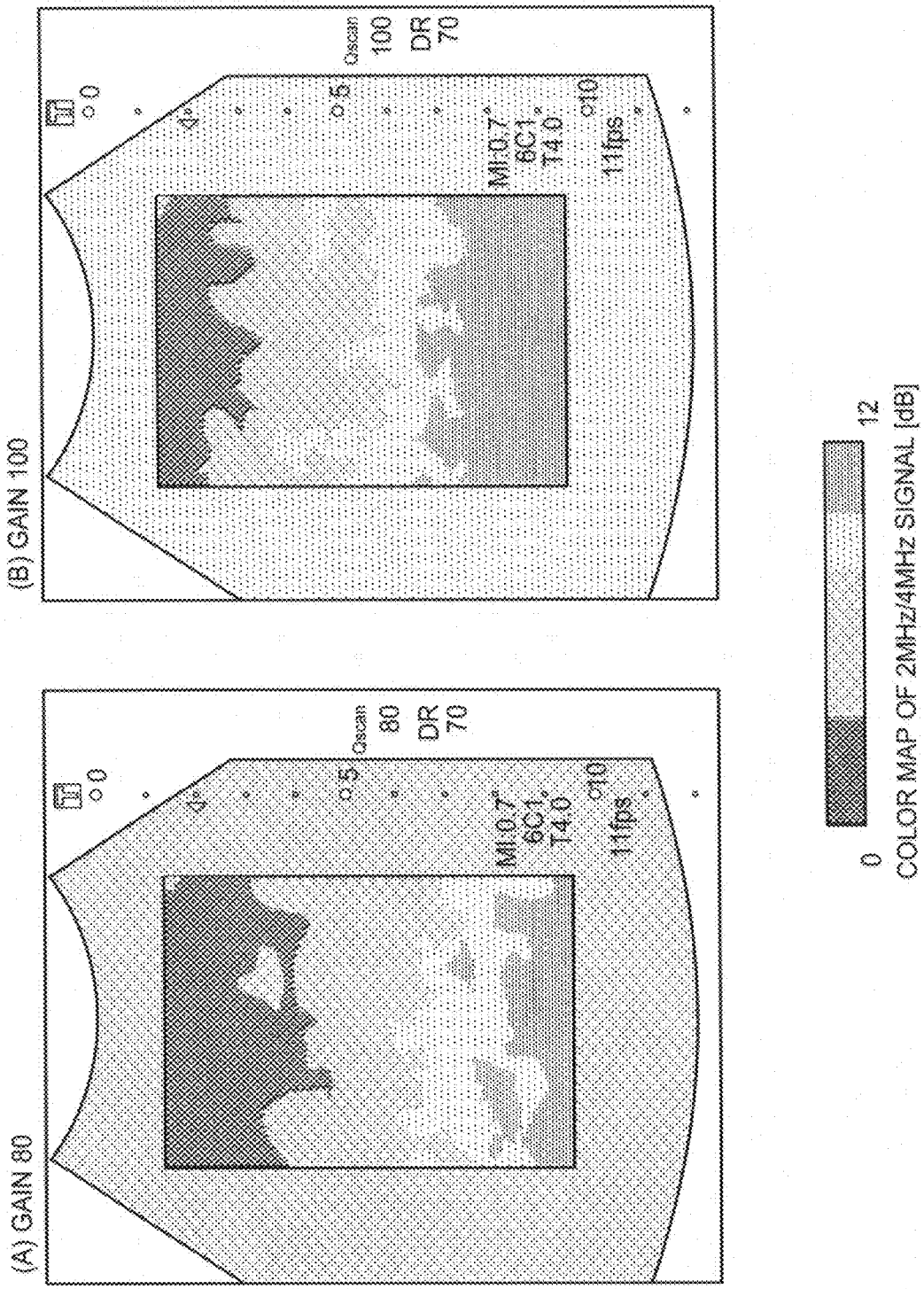
FIG. 2 is a first diagram illustrating a problem with a conventional technology.

FIG. 2 is a first diagram illustrating a problem of the conventional technology. In FIG. 2, a phantom having an attenuation constant "0.5 dB/cm/MHz" is used as a subject and superposed images each of a B-mode image and an attenuation image whose gains are changed are shown. Specifically, a superposed image with a gain of "80" and a superposed image with a gain of "100" are shown. The B-mode image is an image generated by transmitting and receiving an ultrasound signal whose center frequency is "4 MHz". The attenuation image is an image in which the difference in each pixel between the luminance of the B-mode image whose center frequency is "2 MHz" and the luminance of the B-mode image whose center frequency is "4 MHz" is indicated by a color map.

Figure 3:
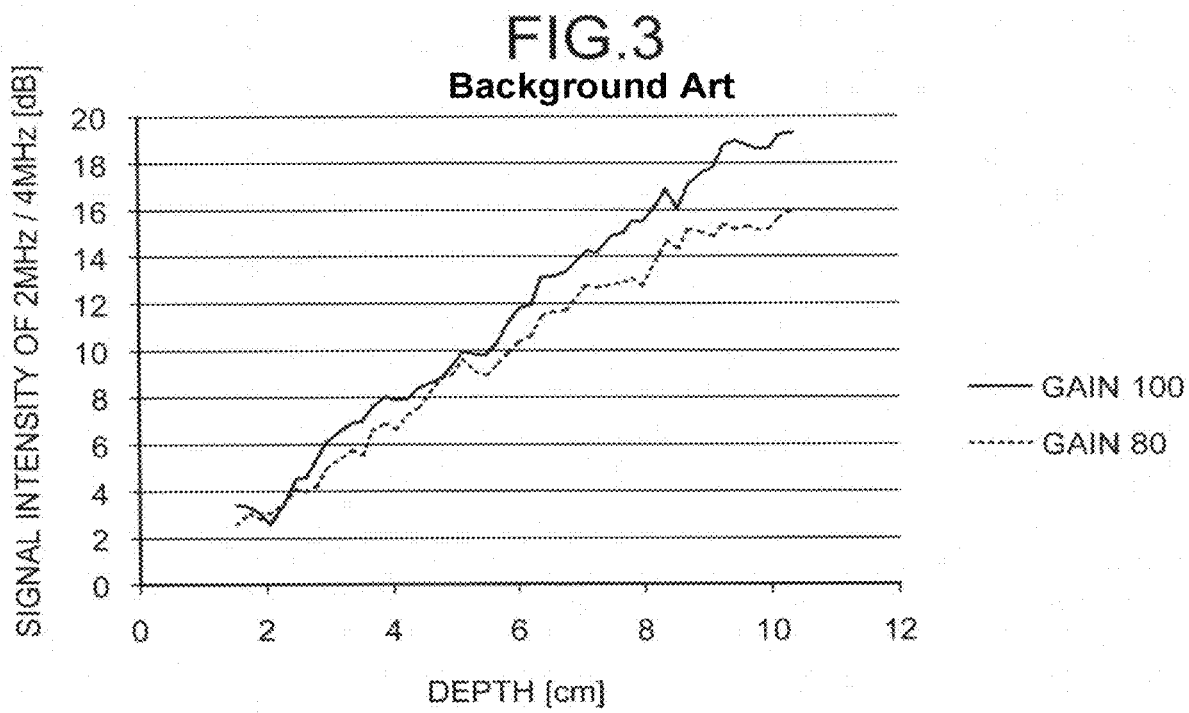
FIG. 3 is a second diagram illustrating the problem of the conventional technology.

As shown in FIG. 2, the color distribution of the attenuation image varies in FIG. 2(A), in which the gain is "80", and in FIG. 2(B), in which the gain is "100". In other words, it is indicated that the measurement result varies if the gain changes. FIG. 3 is a second diagram illustrating the problem of the conventional technology. FIG. 3 indicates a graph in which the values near the center of the attenuation image in FIG. 2(A) and FIG. 2(B) are plotted in the depth direction. As shown in FIG. 3, the value difference between the image with the gain of "80" and the image with the gain of "100" increases as the depth increases from approximately "3 cm". The attenuation constant that is estimated by performing a differentiation on the values between "3 cm" and "9 cm" is "0.49 (dB/cm/MHz)" when the gain is "100" and is, in contrast, "0.42 (dB/cm/MHz)" when the gain is "80". In other words, it is obvious that, when the gain is low, the attenuation constant is underestimated with respect to the real value.

Accordingly, as described above, when the amount of attenuation of an echo signal is quantitatively analyzed and used for a diagnosis, an area in which the S/N is low should be excluded from areas whose amount of attenuation is analyzed. However, in the conventional technology, it cannot be determined which area should be excluded, and thus an area that is difficult to reliably analyze may be analyzed.

In the first embodiment, an area whose S/N is low is extracted and is displayed to the observer under the control of the controller 170 described in detail below so that only areas that can be reliably analyzed can be analyzed.

Figure 4:
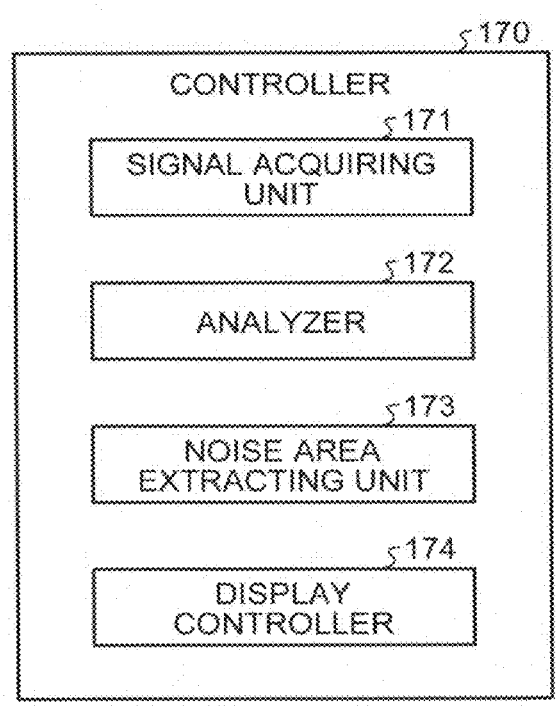
FIG. 4 is a diagram illustrating an exemplary configuration of a controller according to the first embodiment.

FIG. 4 is a diagram illustrating an exemplary configuration of the controller 170 according to the first embodiment. As shown in FIG. 4, the controller 170 includes a signal acquiring unit 171, an analyzer 172, a noise area extracting unit 173, and a display controller 174.

The signal acquiring unit 171 transmits multiple ultrasound signals of different frequencies to a position in the subject and thus acquires multiple received signals. Specifically, the signal acquiring unit 171 controls the ultrasound transmitting unit 110 such that the ultrasound probe 10 transmits multiple ultrasound signals of different frequencies. The signal acquiring unit 171 then controls the ultrasound receiving unit 120 such that it receives signals of the respective frequencies. The signal acquiring unit 171 causes the B-mode processing unit 131 to generate B-mode data of each frequency.

The signal acquiring unit 171 transmits multiple ultrasound signals of different frequencies and thus acquires noise-signal information on each area from which the received signals are acquired. Specifically, while the ultrasound signals transmitted from the ultrasound probe 10 are stopped, the signal acquiring unit 171 acquires, as noise signal information, signals received from each area in the subject. More specifically, while ultrasound waves transmitted from the ultrasound probe 10 are stopped, the signal acquiring unit 171 causes the B-mode processing unit 131 to generate B-mode data of the signal received by the ultrasound receiving unit. Transmitting/receiving of multiple ultrasound signals of different frequencies and receiving of signals while transmitting of signals is stopped may be performed for each frame. Alternatively, transmitting/receiving of high-frequency ultrasound waves, transmitting/receiving of low-frequency ultrasound waves, and receiving of signals while transmitting of signals is stopped may be performed for each raster.

Figure 5:
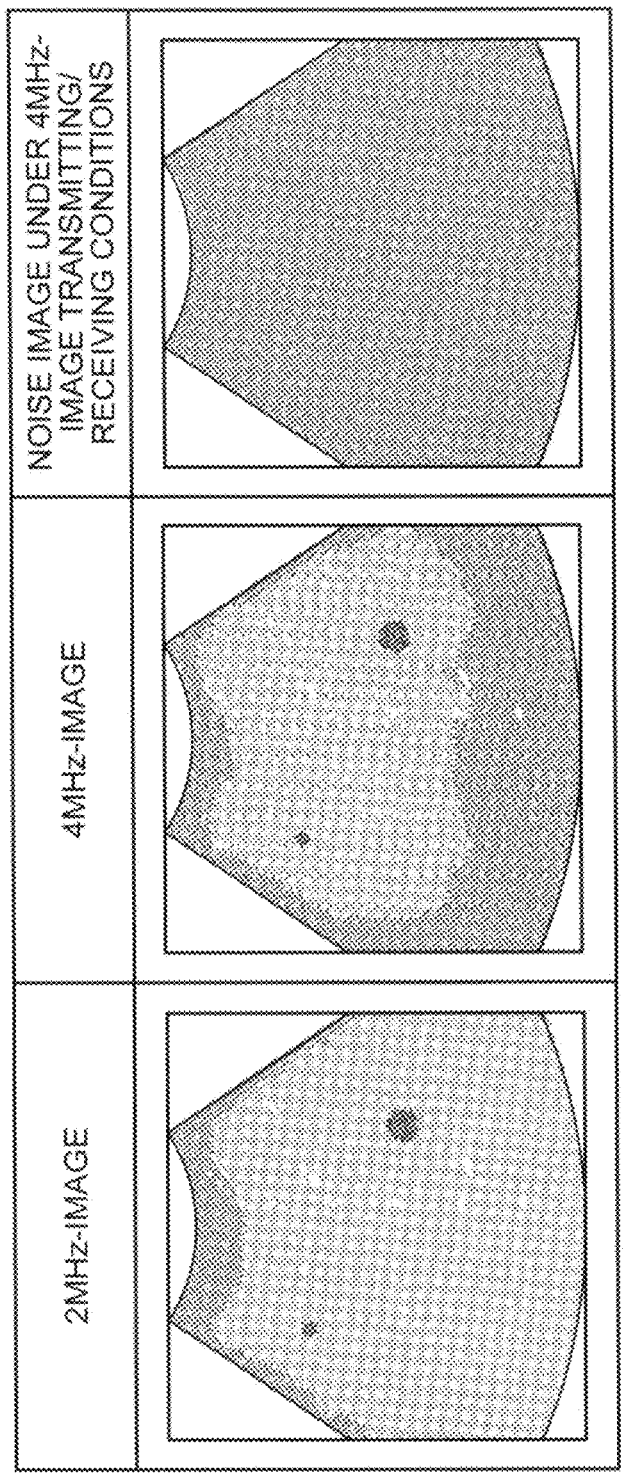
FIG. 5 is a diagram illustrating an exemplary process performed by a signal acquiring unit according to the first embodiment.

FIG. 5 is a diagram illustrating an exemplary process performed by the signal acquiring unit 171 according to the first embodiment. In FIG. 5, B-mode images are shown for descriptive purposes. However, in practice, the signal acquiring unit 171 performs a process in the apparatus and thus the images are not displayed to the observer.

For example, as shown in FIG. 5, the signal acquiring unit 171 transmits/receives ultrasound signals of 2 MHz and 4 MHz in order to generate B-mode images (a 2-MHz image and a 4-MHz image). Furthermore, as shown in FIG. 5, the signal acquiring unit 171 performs only a receiving process under the same condition as that for transmitting/receiving 4-MHz ultrasound signals to generate "noise image under a 4-MHz transmitting/receiving condition" that is a B-mode image generated using the received signal. Here, the same receiving conditions as that for transmitting/receiving 4-MHz ultrasound signals include, for example, performing on the received signal the same filtering as the filtering performed when transmitting/receiving 4-MHz ultrasound signals; and using the same gain. The B-mode images generated under the control of the signal acquiring unit 171 are stored in an image memory 26.

The following section refers back to FIG. 4. The analyzer 172 analyzes, on the basis of the received signals of the ultrasound waves, the tissue state at the position in a subject from which the ultrasound waves that are transmitted by the ultrasound probe 10 into the subject are reflected. Specifically, by using multiple received signals that are obtained by transmitting multiple ultrasound signals of different frequencies to a position in the subject, the analyzer 172 generates a signal reflecting the difference in the amount of attenuation between the received signals resulting from the difference in frequency. More specifically, the analyzer 172 generates an attenuation image in which the luminance difference in each pixel between B-mode images of different frequencies that are generated by the signal acquiring unit 171 and stored in the image memory 26 is color-mapped. The attenuation image that is generated by the analyzer 172 is stored in the image memory 26.

FIG. 6 is a diagram illustrating an exemplary process performed by the analyzer 172 according to the first embodiment. FIG. 6 shows a case in which an attenuation image is acquired by using the "2-MHz image" and the "4-MHz image" shown in FIG. 5. In FIG. 6, B-mode images are shown for descriptive purposes. However, in practice, the analyzer 172 performs the process in the apparatus and thus the images are not displayed to the observer.

For example, the analyzer 172 reads the "2-MHz image" and the "4-MHz image" from the image memory 26 and, as shown in FIG. 6, calculates the difference in each pixel between the luminance of the "2-MHz image" and the luminance of the "4-MHz image", and generates an attenuation image by color-mapping the difference. The analyzer 172 superposes the generated attenuation image on the "4-MHz image".

The following section refers back to FIG. 4. On the basis of noise signal information that is acquired by the signal acquiring unit 171, the noise area extracting unit 173 determines, for each area, whether the received signal used for the analysis by the analyzer 172 is a noise signal. An area on which a determination is made by the noise area extracting unit 173 may be an image pixel or an area including multiple pixels. A case will be described below in which, by using a single pixel, it is determined whether a received signal is a noise signal. Specifically, the noise area extracting unit 173 reads a noise image and an image for a frequency corresponding to the noise image from the image memory 26 and compares the luminance of the noise image and the luminance of the image of the frequency corresponding to the noise image. When they are approximately equal, the noise area extracting unit 173 determines that the luminance of the B-mode image of the frequency corresponding to the noise image results from a noise and extracts the corresponding pixel. The information on the pixel extracted by the noise area extracting unit 173 is stored in the image memory 26.

Figure 7:
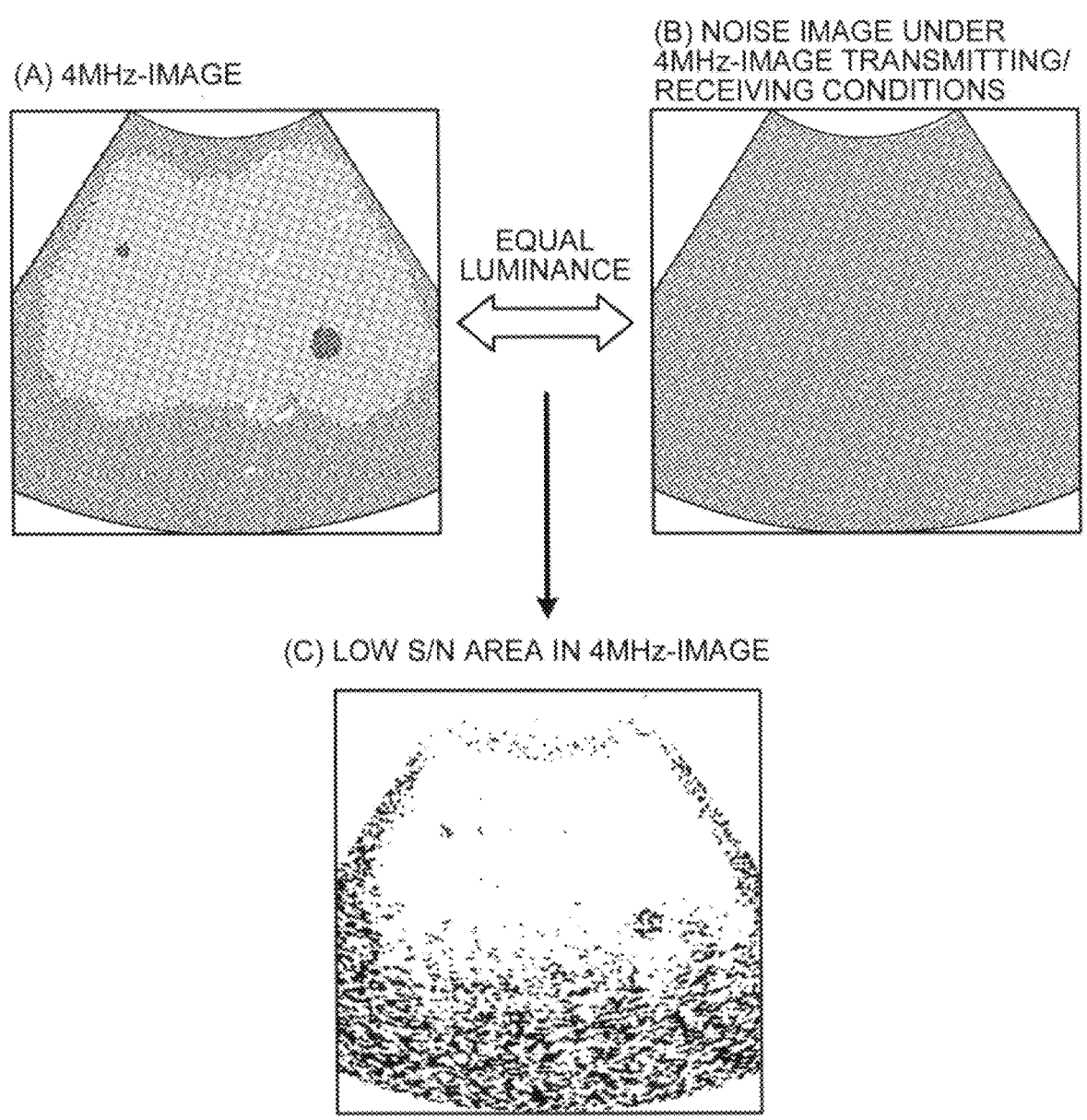
FIG. 7 is a diagram illustrating an exemplary process performed by a noise area extracting unit according to the first embodiment.

FIG. 7 is a diagram illustrating an exemplary process performed by the noise area extracting unit 173 according to the first embodiment. FIG. 7 shows a case in which the "4-MHz image" and the "noise image under a 4-MHz transmitting/receiving condition" that are shown in FIG. 5 are used. In FIG. 7, B-mode images are shown for descriptive purposes. However, in practice, the noise area extracting unit 173 performs the process in the apparatus and thus the images are not displayed to the observer.

For example, as shown in FIG. 7, the noise area extracting unit 173 compares, for each pixel, the luminance of the "4-MHz image" and the luminance of the "noise image under a 4-MHz transmitting/receiving condition" and extracts a pixel with a luminance difference within a predetermined range. As shown in FIG. 7, the noise area extracting unit 173 performs the comparing process on all pixels and extracts all pixels each with a luminance difference within the predetermined range as "low S/N area in the 4-MHz image".

The following section refers back to FIG. 4. When the noise area extracting unit 173 determines that the received signal is a noise signal, the display controller 174 controls the display unit such that it displays the position on which the determination is made. Specifically, the display controller 174 reads an attenuation image and information on a pixel indicating a low S/N area that are stored in the image memory and causes the monitor 30 to display the attenuation image and the information on the pixel indicating the low S/N area.

FIG. 8 is a diagram illustrating an exemplary process performed by the display controller 174 according to the first embodiment. FIG. 8 shows a case in which the "superposed image of the 4-MHz image and the attenuation image" shown in FIG. 6(C) and the "low S/N area in the 4-MHz image" shown in FIG. 7(C) are used.

For example, as shown in FIG. 8(A) and FIG. 8(B), the display controller 174 reads the "superposed image of the 4-MHz image and the attenuation image" that is generated by the analyzer 172 and is stored in the image memory 26 and the "low S/N area in the 4-MHz image" that is extracted by the noise area extracting unit 173 and is stored in the image memory 26. As shown in FIG. 8(C), the display controller 174 then causes the monitor 30 to display a superposed image obtained by superposing the "low S/N area in the 4-MHz image" on the "superposed image of the 4-MHz image and the attenuation image".

For example, when observing the superposed image shown in FIG. 8(C), the observer can determine that the area of the "attenuation image" on which the "low S/N area in the 4-MHz image" is superposed is difficult to reliably analyze. For example, the observer can determine that even an area in the "attenuation image" where the color varies in an approximately equal depth is difficult to reliably analyze if the "low S/N area" is superposed on that area, and thus the area is not used for a diagnosis.

Figures 9, 10:
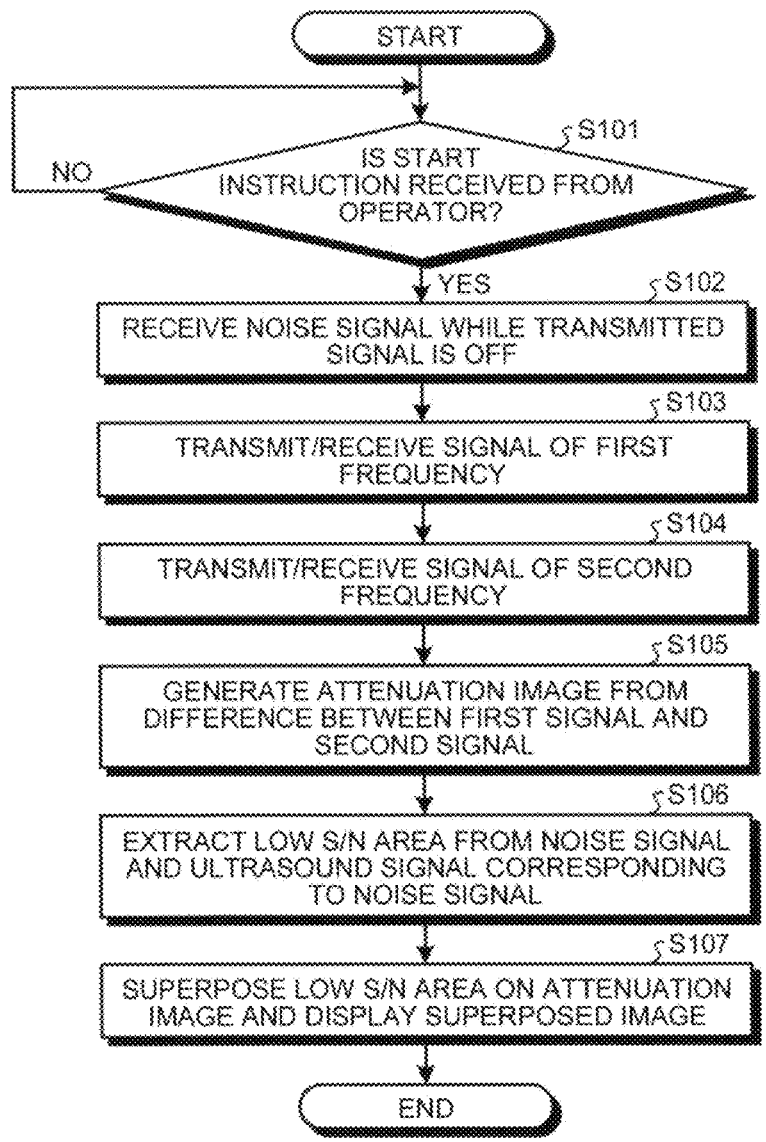
FIG. 9 is a flowchart of a procedure of a process performed by the ultrasound diagnostic apparatus according to the first embodiment.
FIG. 10 is a table regarding exemplary noise signals used by a noise area extracting unit according to a second embodiment.

The process performed by the ultrasound diagnostic apparatus 1 according to the first embodiment will be described using FIG. 9. FIG. 9 is a flowchart of a procedure of the process performed by the ultrasound diagnostic apparatus 1 according to the first embodiment. As shown in FIG. 9, when the ultrasound diagnostic apparatus 1 receives a start instruction from an operator (YES at step S101), the signal acquiring unit 171 causes the ultrasound receiving unit 120 to receive a noise signal while the transmitted signal is off (step S102).

Furthermore, the signal acquiring unit 171 causes the ultrasound transmitting unit 110 and the ultrasound receiving unit 120 to transmit and receive an ultrasound signal of a first frequency among different frequencies (step S103). The signal acquiring unit 171 then causes the ultrasound transmitting unit 110 and the ultrasound receiving unit 120 to receive and transmit an ultrasound signal of a second frequency among different frequencies (step S104).

The analyzer 172 then generates an attenuation image from the difference (ratio) between the first signal and the second signal (step S105). The noise area extracting unit 173 extracts a low S/N area from the noise signal and an ultrasound signal corresponding to the noise signal (step S106).

The display controller 174 causes the monitor 30 to display a superposed image obtained by superposing the low S/N area extracted by the noise area extracting unit 173 on the attenuation image generated by the analyzer 172 (step S107) and ends the process.

Until the ultrasound diagnostic apparatus 1 receives a start instruction, the ultrasound diagnostic apparatus 1 is in standby state (NO at step S101). In the above-described procedure, a case is described in which, after a noise signal is acquired, ultrasound signals of different frequencies are transmitted and received. However, embodiments are not limited to this. A noise signal may be acquired after ultrasound signals of different frequencies are transmitted and received. Regarding FIG. 9, a case is described in which a low S/N area is extracted after an attenuation image is generated, but embodiments are not limited to this. An attenuation image may be generated after a low S/N area is extracted. Alternatively, generation of an attenuation image and extraction of a low S/N area may be simultaneously performed.

As described above, according to the first embodiment, the analyzer 172 analyzes, on the basis of received signals of the ultrasound waves, the tissue state in the position from which the ultrasound waves that are transmitted by the ultrasound probe 10 into the subject are reflected. The signal acquiring unit 171 acquires noise signal information corresponding to an area that is analyzed by the analyzer 172. On the basis of the information on the noise signal acquired by the signal acquiring unit 171, the noise area extracting unit 173 determines, for each area, whether a received signal used for an analysis performed by the analyzer 172 is a noise signal. When the noise area extracting unit 173 determines that the received signal is a noise signal, the display controller 174 controls the monitor 30 such that it displays the area on which the determination is made. Accordingly, the ultrasound diagnostic apparatus 1 according to the first embodiment can indicate a noise area to the observer, and thus, only areas that can be reliably analyzed can be analyzed using physical information contained in an echo signal.

According to the first embodiment, the signal acquiring unit 171 acquires a receiving signal from each area in the subject as information on a noise signal while ultrasounds transmitted from the ultrasound probe 10 are stopped. Accordingly, the ultrasound diagnostic apparatus 1 according to the first embodiment can acquire a noise of the subject easily and accurately.

According to the first embodiment, using multiple received signals that are acquired by transmitting multiple ultrasound waves of different frequencies to a position in the subject, the analyzer 172 generates an attenuation image reflecting the difference in the amount of attenuation between received signals resulting from the frequency difference. Accordingly, the ultrasound diagnostic apparatus 1 according to the first embodiment can reflect frequency-dependent attenuation specific to a tissue across a cross section in an attenuation image and an analysis with high accuracy can be performed.

Second Embodiment

In the first embodiment, a case is described in which a noise signal is acquired in real time. In a second embodiment, a case is described in which noise signal information is acquired previously and the noise signal information is read when a low S/N area is extracted. In the second embodiment, the same configuration as that of the controller 170 according to the first embodiment shown in FIG. 4 is used. In the second embodiment, a controller that reads noise signal information when extracting a low S/N area is described as a signal acquiring unit 171a. In other words, the signal acquiring unit 171a performs a new process in addition to the process performed by the signal acquiring unit 171 shown in FIG. 4.

The signal acquiring unit 171a acquires, from the storage unit 180 that stores previously-acquired noise signal information in association with conditions on transmitting/receiving of ultrasound waves performed by the ultrasound probe 10, noise signal information corresponding to conditions on actual transmitting/receiving of ultrasound waves. Specifically, when a low S/N area is extracted, the signal acquiring unit 171a acquires noise signal information that is stored in association with conditions on transmitting and receiving of a high-frequency ultrasound signal among multiple ultrasound signals of different frequencies that are transmitted/received by the ultrasound probe 10.

FIG. 10 is a table regarding exemplary noise signals acquired by the signal acquiring unit 171a according to the second embodiment. The information shown in FIG. 10 is previously acquired by the operator and stored in the storage unit 180. For example, as shown in FIG. 10, noise signals acquired by the signal acquiring unit 171a according to the second embodiment are stored in association with each transmitting/receiving condition, such as "frequency", "transmission focus", and "gain". The noise signals stored in the storage unit 180 are, for example, noise images under transmitting/receiving conditions.

The signal acquiring unit 171a acquires conditions on transmitting/receiving of a high-frequency ultrasound signal among multiple ultrasound signals of different frequencies that are transmitted/received by the ultrasound probe 10 and reads, from the storage unit 180, a noise signal that is associated with the same transmitting/receiving conditions as the acquired transmitting/receiving conditions. Specifically, the signal acquiring unit 171a reads a noise image that is associated with the same transmitting/receiving conditions as the acquired transmitting/receiving conditions. When extracting a low S/N area, the noise area extracting unit 173 uses the noise image that is read by the signal acquiring unit 171a.

A process performed by the ultrasound diagnostic apparatus 1 according to the second embodiment will be described using FIG. 11. FIG. 11 is a flowchart of a procedure of the process performed by the ultrasound diagnostic apparatus 1 according to the second embodiment. As shown in FIG. 11, when the ultrasound diagnostic apparatus 1 according to the second embodiment receives a start instruction from the operator (YES at step S201), the signal acquiring unit 171a causes the ultrasound transmitting unit 110 and the ultrasound receiving unit 120 to transmit and receive an ultrasound signal of a first frequency among different frequencies (step S202).

The signal acquiring unit 171a then causes the ultrasound transmitting unit 110 and the ultrasound receiving unit 120 to receive and transmit an ultrasound signal of a second frequency among the different frequencies (step S203). Furthermore, the signal acquiring unit 171a reads, from the storage unit 180, noise data (noise image) corresponding to transmitting/receiving conditions (step S204).

The analyzer 172 then generates an attenuation image from the difference (ratio) between the first signal and the second signal (step S205). The noise area extracting unit 173 extracts a low S/N area from the noise signal, which is read by the signal acquiring unit 171a, and an ultrasound signal corresponding to the noise signal (step S206).

The display controller 174 causes the monitor 30 to display a superposed image obtained by superposing the low S/N area extracted by the noise area extracting unit 173 on the attenuation image generated by the analyzer 172 (step S207) and ends the process.

Until the ultrasound diagnostic apparatus 1 receives a start instruction, the ultrasound diagnostic apparatus 1 is in a standby state (NO at step S201). In the above-described procedure, a case is described in which a noise signal is read after ultrasound signals of different frequencies are transmitted and received. However, embodiments are not limited to this. Ultrasound signals of different frequencies may be transmitted and received after a noise signal is read. Regarding FIG. 11, a case is described in which a low S/N area is extracted after an attenuation image is generated; however, embodiments are not limited to this. An attenuation image may be generated after a low S/N area is extracted. Alternatively, generation of an attenuation image and extraction of a low S/N area may be performed simultaneously in parallel.

As described above, according to the second embodiment, the signal acquiring unit 171a acquires conditions on transmitting/receiving a high-frequency ultrasound signal among multiple ultrasound signals of different frequencies that are transmitted and received by the ultrasound probe 10 and reads, from the storage unit 180, a noise signal associated with the same transmitting/receiving conditions as the acquired transmitting/receiving conditions. Accordingly, the ultrasound diagnostic apparatus 1 according to the second embodiment can reduce the process load when performing an analysis.

Third Embodiment

The first and second embodiments are described above. In addition to the first and second embodiments, various different embodiments may be carried out.

(1) Modification 1

In the first and second embodiments, a case is described in which the present method is used to analyze the tissue state according to the amount of attenuation of an ultrasound signal. In Modification 1, a case is described in which the present method is used to analyze the tissue state according to a probability density distribution of the signal intensities of ultrasound signals. Specifically, a case is described in which the present method is applied to a method for quantifying the content of an abnormal structure contained in an area to be diagnosed, which is the method performed by calculating a probability density distribution curve from the signal intensities of the received signals from the area to be diagnosed and by comparing the calculated probability density distribution curve with a probability density distribution curve (for example, Rayleigh distribution) of theoretical values obtained when a site to be diagnosed is healthy.

In Modification 1, the same configuration as that of the controller 170 according to the first embodiment shown in FIG. 4 is employed. In Modification 1, a controller that analyzes the tissue state according to the probability density distribution of the signal intensities of ultrasound signals is described as an analyzer 172a. In other words, the analyzer 172a performs a new process in addition to the process performed by the analyzer 172 shown in FIG. 4.

The analyzer 172a calculates a probability density distribution of the signal intensities of signals received from a site to be diagnosed in a subject and calculates the difference between the calculated probability density distribution and the probability density distribution of theoretical values that are calculated from the signal intensities of received signals obtained when the site to be diagnosed is healthy. Specifically, the analyzer 172a acquires the signal intensity of signals received from an area to be diagnosed and calculates the probability density distribution from the variance and average of the signal intensities of the area to be diagnosed. Here, by displaying a low S/N area to the operator, the operator can extract an area to be diagnosed from a high S/N area. In other words, the probability density distribution that is calculated by the analyzer 172a is reliable.

The analyzer 172a calculates a probability density distribution curve of an area to be diagnosed and a probability density distribution curve of theoretical values. The display controller 174 causes the monitor 30 to display the probability density distribution curve that is calculated by the analyzer 172a. According to the deviation between the two probability density distribution curves displayed on the monitor 30, the operator can estimate the amount of an abnormal structure contained in the area to be diagnosed. For example, as cirrhosis progresses, the number and size of nodules increase in an anatomical view. Using the above-described method of Modification 1 allows a diagnosis with high reliability with regard to such an increase in the number and size of tubers.

(2) Modification 2

In Modification 1, a case is described in which the present method is used to analyze the tissue state by using a probability density distribution of signal intensities of ultrasound signals. In Modification 2, a case will be described in which the present method is applied to analyze the tissue state by tissue Doppler imaging and elastography.

In Modification 2, the same configuration as that of the controller 170 according to the first embodiment shown in FIG. 4 is used. In Modification 2, a controller that analyzes the tissue state by tissue Doppler imaging and elastography is described as an analyzer 172b. In other words, the analyzer 172b performs a new process in addition to the process performed by the analyzer 172 shown in FIG. 4.

The analyzer 172b analyzes the amount of displacement of a local site, the speed of the local site, or stiffness of the local site by using Doppler data from multiple frames. Specifically, the analyzer 172b analyzes the amount of displacement of the local site, the speed of the local site, or stiffness of the local site based on the Doppler data generated by Doppler processing unit 132. For example, the analyzer 172b calculates a phase of each pixel by using speed components, variance components, and power components that are contained in the Doppler data and calculates the strain of a tissue from the calculated phase of each pixel.

The analyzer 172b generates a color map in which the calculated strain is used as the stiffness or elastic modulus of the tissue. The display controller 174 causes the monitor 30 to display the color map that is generated by the analyzer 172b. Displaying a low S/N area in a different color allows the operator to analyze only areas that can be analyzed reliably.

(3) Noise Image

In the first and second embodiments, a case is described in which a noise image corresponding to a high-frequency ultrasound signal is acquired. However, embodiments are not limited to this. For example, a noise image corresponding to a low-frequency ultrasound signal may be acquired in addition to the noise image corresponding to the high-frequency ultrasound signal.

(4) Used Signal

In the first and second embodiments, a case is described in which a B-mode image is generated using B-mode data that is generated by the B-mode processing unit and an analysis is performed using the generated B-mode data.

However, embodiments are not limited to this. For example, raw data or B-mode data that is generated by the ultrasound receiving unit may be used.

(5) Area

In the first and second embodiments, a case is described in which, by comparing, for each single pixel, the luminance of a noise image and the luminance of an image of a frequency corresponding to the noise image, it is determined whether the luminance of the image of the frequency corresponding to the noise image is noise. However, embodiments are not limited to this. For example, it may be determined whether the luminance is noise by using a pixel area including multiple pixels. In an example, such a determination may be made by using the luminance of pixels around a pixel on which a determination is made on whether the luminance is noise (for example, surrounding 8 pixels).

In such a case, the noise area extracting unit 173 reads, from the image memory 26, a noise image and an image of a frequency corresponding to the noise image. The noise area extracting unit 173 calculates the luminance of a pixel on which a determination is made and an average of the luminances of the 8 surrounding pixels for each of the noise image and the image of the frequency corresponding to the noise image. When the average luminance in the noise image and the average luminance in the image of the frequency corresponding to the noise image are approximately equal (if the average difference is within a predetermined range), the noise area extracting unit 173 determines that the luminance of the B-mode image of the frequency corresponding to the noise image is the luminance resulting from the noise and extracts the corresponding pixel.

(6) Target Image

In the first and second embodiments, a case is described in which images of different frequencies (2 MHz and 4 MHz) are analyzed. However, embodiments are not limited to this. For example, images of a single frequency may be analyzed. For example, only a 4-MHz B-mode image may be used.

(7) Display Method

In the first and second embodiments, a case is described in which a low S/N area is displayed in a different color. However, embodiments are not limited to this. For example, control may be performed such that an image analysis result, such as a tissue state analysis result, is not displayed as being superposed on an area that is determined as a low S/N area.

As described above, according to the first embodiment, the second embodiment, and the third embodiment, the ultrasound diagnostic apparatus according to the embodiments can analyze an area that can be analyzed reliably using physical information contained in an echo signal.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnostic apparatus, comprising:
processing circuitry configured to
determine a low signal/noise (S/N) area in a predetermined area included in a scan area by comparing a pixel intensity of an image generated based on a first echo signal, which was acquired by transmitting and receiving a first ultrasound wave in the scan area, with a pixel intensity of a noise image generated based on a noise signal;
generate a color image showing a stiffness or elasticity within the predetermined area, based on an analysis result of a second echo signal that was acquired by transmitting and receiving a second ultrasound wave in the scan area;
generate a superposed image by superposing the color image on the predetermined area in the image generated based on the first echo signal; and
cause a display to display the superposed image, and further display a position of the determined low S/N area in the superposed image so as to be distinguishable from a region other than the determined low S/N area.

2. The ultrasound diagnostic apparatus according to claim 1, wherein the processing circuitry is further configured to acquire, as the noise signal, a received signal from the scan area while all transmission from an ultrasound probe is stopped, at a timing different from the transmitting/receiving of the first ultrasound wave and the second ultrasound wave.

3. The ultrasound diagnostic apparatus according to claim 1, wherein the processing circuitry is further configured to acquire, from a memory storing previously-acquired noise signal information in association with conditions on transmitting/receiving of various ultrasound waves by an ultrasound probe, the noise signal, which corresponds to particular conditions on transmitting/receiving of the first ultrasound wave.

4. The ultrasound diagnostic apparatus according to claim 3, wherein
the memory is further configured to store a previously-acquired plurality of noise signals for conditions of transmitting/receiving of an ultrasound wave; and
the processing circuitry is further configured to select the noise signal corresponding to conditions on transmitting/receiving of the first ultrasound wave among the previously-acquired plurality of noise signals.

5. The ultrasound diagnostic apparatus according to claim 1, wherein the color image is an elastography image showing the stiffness or elasticity in the predetermined area.

6. A method, comprising:
determining a low signal noise (S/N) area in a predetermined area included in a scan area by comparing a pixel intensity of an image generated based on a first echo signal, which was acquired by transmitting and receiving a first ultrasound wave in the scan area, with a pixel intensity of a noise image generated based on a noise signal;
generating a color image showing a stiffness or elasticity within the predetermined area, based on an analysis result of a second echo signal that was acquired by transmitting and receiving a second ultrasound wave in the scan area;
generating a superposed image by superposing the color image on the predetermined area in the image generated based on the first echo signal; and
causing a display to display the superposed image, and further display a position of the determined low S/N area in the superposed image so as to be distinguishable from a region other than the determined low S/N area.

7. An ultrasound diagnostic apparatus, comprising:
processing circuitry configured to
determine a low signal/noise (S/N) area in a predetermined area included in a scan area by comparing a pixel intensity of an image generated based on a first echo signal, which was acquired by transmitting and receiving a first ultrasound wave in the scan area, with a pixel intensity of a noise image generated based on a noise signal;

generate a color image showing attenuation within the predetermined area, based on an analysis result of a second echo signal that was acquired by transmitting and receiving a second ultrasound wave in the scan area;

generate a superposed image by superposing the color image on the predetermined area in the image generated based on the first echo signal; and cause a display to display the superposed image, and further display a position of the determined low S/N area in the superposed image so as to be distinguishable from a region other than the determined low S/N area.

8. An ultrasound diagnostic apparatus, comprising:
processing circuitry configured to determine a low signal/noise (S/N) area in a predetermined area included in a scan area based on a pixel intensity of an image generated based on a first echo signal;

generate a color image showing a stiffness or elasticity within the predetermined area, based on an analysis result of a second echo signal that was acquired by transmitting and receiving a second ultrasound wave in the scan area;

generate a display image including the color image and the image generated based on the first echo signal, the color image being located in the predetermined area in the image generated based on the first echo signal; and cause a display to display the display image, and further display a position of the determined low S/N area in the display image so as to be distinguishable from a region other than the determined low S/N area.

* * * * *